United States Patent [19]

Jiang

[11] Patent Number: 4,602,013

[45] Date of Patent: Jul. 22, 1986

[54] SUBSTITUTED 2-AMINO-4(1H)PYRIDONES, 7-PYRROLO[1,2-A]PYRIDINONES, 2-QUINOLIZINONES, 7-THIAZOLO[3,2-A]PYRIDINONES AND 2-PYRIDO[1,2-A]AZEPINONES AS VASODILATORS AND BRONCHODILATORS

[75] Inventor: Jack B. Jiang, Neshanic Station, N.J.

[73] Assignee: Ortho Pharmaceutical Corporation, Raritan, N.J.

[21] Appl. No.: 578,259

[22] Filed: Feb. 8, 1984

[51] Int. Cl.[4] .................... A61K 31/55; C07D 221/04
[52] U.S. Cl. .................................... 514/214; 514/226; 514/299; 514/301; 514/306; 514/352; 514/353; 546/297; 546/138; 546/114; 546/183; 544/47; 260/244.4
[58] Field of Search ............... 546/114, 138, 183, 297; 544/47; 514/214, 226, 299, 301, 306, 352, 353; 260/244.4

[56] References Cited

U.S. PATENT DOCUMENTS 3,334,091  8/1967  Houlihan .............................. 544/47
4,288,438  9/1981  Kubo et al. ...................... 260/244.4

FOREIGN PATENT DOCUMENTS 221329  4/1958  Australia ............................ 546/297
73999   3/1983  European Pat. Off. ............ 546/297

OTHER PUBLICATIONS

Kappe et al., Monatsh. Chem., 1983, 114(8-9), pp. 953-963, Abstracted by Chem. Abstracts vol. 100: 51410z, (1984).

"A Guide to the Chemical Basis of Drug Design", by Alfred Burger, John Wiley & Sons, New York, pp. 134-138, (1983), Section 3.11-3.11.1.

Drugs of the Future, "Biologically Active 1,4-Dihydropyridine Derivatives", vol. VI, No. 7, 1981, J. Prous et al.

Vinick et al., Tetrehedron Letters, N044, pp. 4221-4224, (1978), discloses several 4(1H)-pyridones.

Primary Examiner—Donald G. Daus
Assistant Examiner—William A. Teoli, Jr.
Attorney, Agent, or Firm—David J. Levy; Geoffrey G. Dellenbaugh

[57] ABSTRACT

Substituted 2-amino-4(1H)pyridones are provided which are renal vasodilators and bronchodilators.

18 Claims, No Drawings

SUBSTITUTED 2-AMINO-4(1H)PYRIDONES, 7-PYRROLO[1,2-A]PYRIDINONES, 2-QUINOLIZINONES, 7-THIAZOLO[3,2-A]PYRIDINONES AND 2-PYRIDO[1,2-A]AZEPINONES AS VASODILATORS AND BRONCHODILATORS

FIELD OF THE INVENTION

This invention is related to substituted 4-pyridones and particularly to substituted 4-pyridones having an amino or substituted amino substituent in the 2-position.

BACKGROUND OF THE INVENTION

Several 4(1H)-pyridones have been described by Vinick, et al., Tetrahedron Letters, No. 44, Pages 4221-4224 (1978), but no pharmaceutical properties were disclosed for these compounds.

The compounds of the present invention differ from the referenced Vinick compounds principally in having a fused ring system and in their unexpected activity as renal vasodilators and bronchodilators.

SUMMARY OF THE INVENTION

The present invention is concerned with substituted 4-pyridones having the formula:

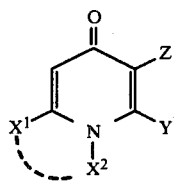

(I)

and the pharmaceutically acceptable acid addition salts and stereochemically isomeric forms thereof, wherein $X^1$ and $X^2$ are individually each loweralkyl or together as $—X^1—X^2—$ are $—(CH_2)_n—$ or $—S—(CH_2)_m—$;

n is 3, 4, or 5;

m is 2 or 3;

Y is amino, loweralkylamino, diloweralkylamino, amido, imido, loweralkyloxyamido, ureido, di(phenylloweralkyl)amino, (diloweralkylamino)methylenamino, or (diloweralkylamino)loweralkylmethylenamino; and Z is hydrogen, loweralkyl, halo, or phenylloweralkyl.

As used in the foregoing definitions, the term "loweralkyl" is meant to include straight and branched saturated hydrocarbon radicals having from one to six carbon atoms, such as for example, methyl, ethyl, 1-methylethyl, 1,1-dimethylethyl, propyl, butyl, pentyl, hexyl, and the like. The term "halo" includes fluoro, chloro, bromo, and iodo.

Preferred compounds of the invention are: those wherein $—X^1—X^2—$ is $—(CH_2)_n—$, n is 4 or 5, Y is amino or diloweralkyl amino, and Z is hydrogen or loweralkyl; those wherein $—X^1—X^2—$ is $—S—(CH_2)_m—$, m is 2, Y is amino, diloweralkylamino, (diloweralkylamino)methylenamino, or (diloweralkylamino)loweralkylmethylenamino, and Z is hydrogen.

More preferred compounds are those wherein $—X^1—X^2—$ is $—(CH_2)_n—$, n is 5, Y is amino or diloweralkylamino, and Z is hydrogen or loweralkyl.

Particularly preferred compounds are 4-amino-7,8,9,10-tetrahydro-6H-pyrido[1,2-a]azepin-2-one and 4-amino-7,8,9,10-tetrahydro-3-methyl-6H-pyrido[1,2-a]azepin-2-one.

The compounds of formula (I) wherein Y is $NH_2$, designated as the compounds of formula (Ia), can generally be prepared by reacting an intermediate of formula (II) with a stoichiometric equivalent of an intermediate of formula (III) according to the reaction:

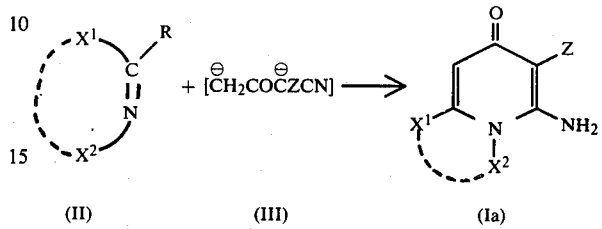

(II)    (III)    (Ia)

wherein X and Z are as defined above and R is a suitable leaving group, such as loweralkoxyl, loweralkylthio, or halo. This reaction may be conducted in a suitable, inert, organic solvent, such as tetrahydrofuran, hexanes, ether, or a combination of these solvents. The intermediate of formula (III) is conveniently formed in situ by the action of lithium diisopropylamide on an appropriately substituted 5-methylisoxazole in a dry inert organic solvent as indicated above. This reaction is preferably conducted under a dry atmosphere and at reduced temperatures.

Following the in situ preparation of intermediate (III), intermediate (II) may be added and the whole is allowed to react. The reaction mixture is thereafter quenched, for example by addition of an alcohol, such as methanol. The resulting product may be converted into its acid addition salt by treatment with the appropriate acid if desired.

The above preparative process yields the compounds of formula (I) wherein Y is $NH_2$. Those compounds of formula (I) wherein Y is other than $NH_2$, designated as the compounds of formula (Ib), may be prepared by reacting the compounds of formula (Ia) with an appropriate N-substituting group Q as set out below. These latter compounds are referred to herein as the compounds of formula (Ib).

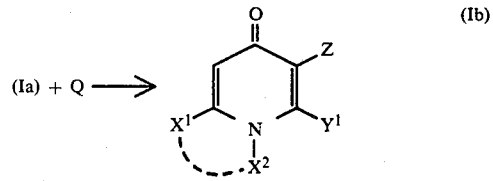

(Ib)

As used herein $Y^1$ may be all values of Y other than $NH_2$ and Q is an N substituting group. When $Y^1$ is loweralkyl-or diloweralkylamino, Q may be for example loweralkyl bromide or loweralkyl iodide; when $Y^1$ is (diloweralkylamino)methylenamino, Q may be for example N,N-diloweralkylformamide diloweralkylacetal; when $Y^1$ is (diloweralkylamino)loweralkylmethyleneamino, Q may be for example (loweralky O)$_2$C-(loweralkyl)N(loweralkyl)$_2$; and when $Y^1$ is amido or imido, Q may be for example acid anhydride. Those skilled in the art will readily understand how to select the appropriate Q group to obtain the desired $Y^1$ group.

In all of the foregoing description and in the following preparations, the reaction products may be isolated from the reaction mixture and, if necessary or desired, further purified according to methodologies generally known in the art.

The intermediates of formula (II) are generally known in the art or may be prepared according to art-known techniques. Such techniques are described, for example, in Oishi, et al., Chem. Pharm. Bull., 17, 2306–2313 (1969), Wick, et al., Helv. Chim. Acta., 54, 513–521 (1971), and Coppola and Damon, J. Heterocyclic Chem., 17, 1729–1731 (1980). The intermediates of formula (III) and methods for preparing them are disclosed in the above-referenced Tetrahedron Letters article.

The compounds of formula (I) have basic properties and therefore may be converted from the free bases to the therapeutically active, non-toxic acid addition salts by treatment with appropriate acids. Suitable inorganic acids are, for example, a hydrohalic acid, such as hydrochloric, hydrobromic, and the like; sulfuric acid, nitric acid, phosphoric acid, and the like. Appropriate organic acids include, for example, acetic, propanoic, hydroxyacetic, 2-hydroxypropanoic, 2-oxopropanoic, propanedioic, butanedioic, (Z)-2-butenedioic, (E)-2butenedioic, 2-hydroxybutanedioic, methanesulfonic, ethanesulfonic, benzenesulfonic, cyclohexanesulfanic, and the like organic acids. Conversely, the salt form may be converted by treatment with a suitable base (e.g., alkali such as sodium hydroxide) into the free base form.

The useful renal vasodilating and bronchodilating properties of the compounds of formula (I) and their acid addition salts are illustrated in the following canine renal vascular resistance test and guinea pig lung anaphylaxis test, respectively. The former test has been described by Goldberg, et al., J. Pharmcol. Exp. Ther., 163, 188 (1968), while the latter test is described by Ritchie, et al., Agents and Actions, 11, 4 (1981). Activity in these tests is well correlated with effectiveness as a renal vasodilator or bronchodilator, respectively.

In the canine renal vascular resistance test, adult mongrel dogs are anesthetized and surgically prepared for electromagnetic measurements of renal artery blood flow. A carotid artery is cannulated for measuring arterial blood pressure. The test drug is administered intravenously or intraarterially (in the renal artery). The heart rate is monitored by a cardiotachometer; renal vascular resistance is calculated as the ratio of mean arterial blood pressure/renal artery blood flow. Initially, dopamine is infused intavenously at 3μg/kg/min for ten minutes (1 ml/min) to determine the responsiveness of each test dog to renal dopamine receptor stimulation. Thereafter, cumulative dose-response data are obtained by infusing the test drug at progressively increasing (usually three fold increasing) infusion rates, each dose being infused for five minutes. The maximum percent increase from pre-drug control in renal artery blood flow (or decrease in renal vascular resistance) is determined for each infusion dose.

In the guinea pig lung anaphylaxis test, male Hartley guinea pigs are actively sensitized by injecting them i.p. with one mg ovalbumin in 16 mg alum. Fourteen days after being sensitized, these animals are anesthetized and are treated with succinylcholine to arrest their respiration. Respiration is maintained at a constant pressure by a miniature Startling pump. Lung overflow changes in pressure are recorded.

The test animals are initially pretreated with indomethacin (10 mg/kg, i.v.) atropine (0.5 mg/kg, i.v.), methysergide (0.1 mg/kg, i.v.), methapyrilene (2.0 mg/kg, i.v.), and arachidonic acid (5.0 mg/kg, i.v.) prior to the ovalbumin challenge. The test compound is administered between the pretreatment and the ovalbumin challenge. The activity of the test compound is demonstrated as a reduction in the degree of bronchoconstriction due to ovalbumin-induced analphalaxis, as compared to that observed in the control animals. The bronchoconstriction (BC) is measured as a percent of maximum bronchoconstriction obtained by clamping off the trachea. Percent inhibition as compared to control is determined by the following formula:

$$\% \text{ Inhibition} = \frac{\text{control } \% \text{ BC} - \text{treated } \% \text{ BC}}{\text{control } \% \text{ max } BC} \times 100$$

Test results for exemplary compounds of formula (I) are provided in Tables 1 and 2 below. These results are given not for the purpose of limiting the invention thereto, but only to exemplify the useful pharmacological activities of all the compounds within the scope of formula (I).

TABLE 1

Results of the Canine Vascular Resistance Test

| X | Y | Z | Salt | RBF/RVR 13.9 mpk, i.v. | |
|---|---|---|------|------------------------|---|
| —(CH$_2$)$_4$— | NH$_2$ | H | HCl | 28/−15 | |
| —(CH$_2$)$_5$— | NH$_2$ | H | HCl | 30/−22 | (30 mpk) |
| —(CH$_2$)$_4$— | N(CH$_3$)$_2$ | H | HCl | 17/−19 | |
| —(CH$_2$)$_5$— | N(CH$_3$)$_2$ | H | — | 26/−24 | |
| —(CH$_2$)$_5$— | N(CH$_3$)$_2$ | H | HCL | 22/−14 | (20/−20, 5 mpk, p.o.) |
| —(CH$_2$)$_5$— | N(CH$_2$CH$_2$CH$_3$)$_2$ | H | HBr | 14/−14 | |
| —(CH$_2$)$_5$— | NH$_2$ | CH$_3$ | HCl | 9/−13 | |
| —(CH$_2$)$_5$— | N(CH$_2$Ph)$_2$ | PhCH$_2$ | HCl | 18/−16 | |
| —(CH$_2$)$_5$— | O<N(CH$_2$CH=CH$_2$) | H | — | 28/−22 | |
| —(CH$_2$)$_3$— | N=C(CH$_3$)N(CH$_3$)$_2$ | H | — | 6/−4 | |
| —(CH$_2$)$_4$— | N=CHN(CH$_3$)$_2$ | H | — | 12/−15 | |
| —(CH$_2$)$_5$— | N=CHN(CH$_3$)$_2$ | H | — | 18/−16 | |
| —(CH$_2$)$_5$— | N=C(CH$_3$)N(CH$_3$)$_2$ | H | — | 14/−13 | |
| —S(CH$_2$)$_2$— | N=CHN(CH$_3$)$_2$ | H | — | 33/−27 | |
| —S(CH$_2$)$_2$— | N=C(CH$_3$)N(CH$_3$)$_2$ | H | — | 53/−34 | |
| —(CH$_2$)$_4$— | N=C(CH$_3$)N(CH$_3$)$_2$ | H | — | 15/−9 | |
| —(CH$_2$)$_4$— | NH$_2$ | CH$_3$ | HCl | 16/−11 | |
| —S(CH$_2$)$_2$— | N(CH$_3$)$_2$ | CH$_3$ | HCl | 12/−9 | |
| —(CH$_2$)$_5$— | N(CH$_3$)$_2$ | Br | HCl | 10/−17 | |
| —S(CH$_2$)$_2$— | N(COCH$_3$)$_2$ | H | — | 14/−9 | (6.20 mpk) |

TABLE 2

Results of the Guinea Pig Lung Anaphalaxis Test

| X | Y | Z | Salt | %, 50 mpk, i.p. | |
|---|---|---|------|-----------------|---|
| $-(CH_2)_3-$ | $NH_2$ | H | HCl | 45 | |
| $-S(CH_2)_2-$ | $NH_2$ | H | — | 30.4 | |
| di-$CH_3-$ | $NH_2$ | H | HCl | 44.9 | (i.v.) |
| $-(CH_2)_4-$ | $N(CH_3)_2$ | H | — | 66.10 | (10 mpk, i.v.) |
| $-S(CH_2)_2-$ | $N(CH_3)_2$ | H | HCl | 51.4 | (i.v.) |
| $-(CH_2)_4-$ | $N(C_2H_5)_2$ | H | HBr | 40.0 | |
| $-(CH_2)_5-$ | $N=CHN(CH_3)_2$ | H | — | 50.5 | |
| $-(CH_2)_5-$ | $N=C(CH_3)N(CH_3)_2$ | H | — | 27.5 | |
| di-$CH_3-$ | $N=CHN(CH_3)_2$ | H | — | 21.7 | |
| $-(CH_2)_5-$ | $N(CH_3)_2$ | $CH_3$ | HCl | 54.2 | |
| $-(CH_2)_5-$ | $NH_2$ | $CH_3$ | HCl | 87.0 | |
| $-(CH_2)_4-$ | $NH_2$ | $CH_3$ | HCl | 50.0 | |
| $-(CH_2)_4-$ | $N(CH_3)_2$ | $CH_3$ | HCl | 21.0 | |
| $-(CH_2)_5-$ | $NHCOCH_3$ | H | — | 48.2 | (i.v.) |

The compounds of formula (Ia) are additionally useful as intermediates for preparation of pharmaceutically useful compounds.

In view of their renal vasodilating and bronchodilating properties, the compounds of formula (1) and their acid addition salts are useful in the treatment of hypertension and bronchial asthma, respectively.

To prepare the pharmaceutical compositions of this invention, an effective amount of the particular compound, in free base or acid addition salt form, is combined as the active ingredient in intimate admixture with a pharmaceutically acceptable carrier, which carrier may take a wide variety of forms depending on the form of preparation desired for administration.

These pharmaceutical compositions are desirably in unitary dosage form, preferably suitable for administration orally, rectally, or by parenteral injection. For example, in preparing the co:epositions in oral dosage form, any of the usual pharmaceutical media may be employed, such as for example water, glycols, oils, alcohols, and the like in the case of oral liquid preparations, such as suspension, syrups, elixirs, and solutions; or solid carriers, such as starches, sugar, kaolin, lubricants, binders, disintegrating agents, and the like in the case of powders, pills, capsules, tablets, or the like oral solid preparations. Because of their ease in administration, tablets and capsules represent the most advantageous oral dosage unit form, in which case solid pharmaceutical carriers are obviously employed. For parenteral compositions, the carrier will usually comprise sterile water, at least in large part, although other ingredients (e.g., to aid solubility) may be included. Injectable solutions may be prepared, for example, in which the carrier comprises saline solution, glucose solution, or a mixture of saline and glucose solution. Injectable suspensions :nay also be prepared in which case appropriate liquid carriers, suspending agents, and the like may be employed.

Acid addition salts of (I) are obviously more suitable in the preparation of aqueous compositions due to their increased water solubility over the corresponding free base form.

It is especially advantageous to formulate the aforementioned pharmaceutical compositions in dosage unit form for ease of administration and uniformity of dosage. The term "dosage unit form" as used in the specification and claims herein, refers to physcially discrete units suitable as unitary dosages, each unit containing a pre-determined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls, and the like, and segregated multiples thereof.

The present invention also provides a method of treating hypertension in a warm-blooded animal (including man) suffering from hypertension by administering to the subject in need of same an effective antihypertensive amount of a compound of formula (I) or a pharmaceutically acceptable acid addition salt thereof. The present invention further provides a method of treating bronchial asthma in a warm-blooded animal suffering from bronchial asthma by administering to the subject in need of same an effective anti-asthma amount of a compound of formula (I) or a pharmaceutically acceptable acid addition salt thereof.

Suitable doses for treatment of hypertension range from about 5 mg/kg through about 30 mg/kg of body weight, while suitable doses for treatment of bronchial asthma range from about 10 mg/kg to about 50 mg/kg body weight.

The following examples are intended to illustrate and not to limit the scope of the present invention. Unless otherwise note herein all parts are by weight.

EXAMPLE I

5-Amino-2,3-dihydro-1H-indolizin-7-one Monohydrochloride

To a solution of lithium diisopropylamide (LDA), prepared from n-BuLi (125 ml, 0.2M) and diisopropylamine (20.24 g, 0.2M), in dry THF (200 ml) was added under $N_2$ at $-10°$ C. 5-methylisoxazole (8.31 g, 0.1 M). The resultant yellow suspension was stirred at $-10°$ C. for 1 hr before 1-aza-2- methoxy-1-cyclopentene (9.9 g, 0.1M) was added dropwise. A light yellow precipitate was immediately formed. The mixture was allowed to warm to ambient over a period of 19 hr. MeOH (100 ml) was slowly added with external cooling so that the internal temperature remained at $25°-26°$ C. The resulting reddish solution was then stirred at ambient for 24 hr and evaporated in vacuo. Flash column chromatography (30% MeOH in $CH_2Cl_2$ on silica gel, Em-60) followed by recrystallization (MeOH/$Et_2O$) gave the desired free base (3 g, 20%); mp>230° C. It was then transformed into its HCl salt in MeOH with conc HCl. The salt was further recrystallized from MeOH/$Et_2O$ to yield the title compound; mp>250° C. yield 3 g, 81%); TLC (30% MeOH in $CH_2Cl_2$); Rf=0.37; IR (KBr) cm$^{-1}$, 3500, 3140, 1670, 1590.

Anal. Calcd for $C_8H_{10}N_2O \cdot HCl$: C, 51.48; H, 5.94; N, 15.01. Found: C, 51.08; H, 5.77; N, 14.89.

EXAMPLE II

4-Amino-6,7,8,9-tetrahydroquinolizin-2-one Monohydrochloride

To a solution of lithium diisopropylamide (LDA), prepared from n-BuLi (64.5 ml, 0.1M) and diisopropylamine (10.1 g, 14 ml, 0.1M) in dry THF (100 ml) was added under $N_2$ at $-10°$ C. 5-methylisoxazole (4.2 g, 4.1 ml, 0.05M). The resultant yellow suspension was stirred (mechanical stirrer) at $-10°$ C. for 1 hr before 1-aza-2-methoxy-1-cyclohexene (5.6 g, 0.05M) was added dropwise. A light yellow precipitate was immediately formed. The mixture was allowed to warm to ambient over a period of 20 hr. MeOH (40 ml) was slowly added and the resulting reddish solution was stirred at ambient for 2 hr. The solvents were evaporated in vacuo, and the residual oil was flash column chromatographed on silica gel (EM-60) with 30% MeOH in $CH_2Cl_2$ as the eluent to give the desired free base. The HCl salt was then prepared by adding conc HCl to a solution of the free base in methanol. Recrystallization from MeOH/ether gave the title compound (2.9 g, 29%). TLC (30% MeOH in $CH_2Cl_2$); Rf=0.53. IR (KBr), cm$^{-1}$, 3330, 3180, 3030, 2950.

Anal. Calcd for $C_9H_{12}N_2O \cdot HCl$: C, 53.87; H, 6.53; N, 13.96. Found: C, 53.75; H, 6.46; N, 13.96.

EXAMPLE III

5-Amino-2,3-dihydrothiazolo[3,2-a]pyridin-7-one

To a solution of lithium diisopropylamide (LDA), prepared from n-BuLi (106.6 ml, 0.16M) and diisopropylamine (16.7 g, 23.1 ml, 0.16M), in dry THF (100 ml) was added under $N_2$ at $-10°$ C., 5-methylisoxazole (6.8 g, 0.08M). The resultant yellow suspension was mechanically stirred at $-10°$ C. for 30 min before the 4,5-dihydro-2-methylthiothiazole (11 g, 0.08M) was added dropwise. After the addition was complete, an orange oil separated, and the mixture was allowed to warm to ambient over a period of 20 hr. A mixture of MeOH (60 ml) and glacial acetic acid (4.5 ml, 0.08M) was slowly added and the resultant reddish solution was stirred at ambient overnight. The solvents were evaporated in vacuo, and the residual oil was flash column chromatographed on silica gel (EM-60) with 30% MeOH in $CH_2Cl_2$ as the eluent to give the desired amine (7 g), which was further recrystallized from MeOH-/Et$_2$O to give the title compound (5.4 g, 40%), mp>241° C. TLC (30% MeOH in $CH_2Cl_2$); Rf=0.33. IR (KBr) cm$^1$, 3350–3000 (broad), 1675, 1625.

Anal. Calcd for $C_7H_8N_2OS$: C, 49.98; H, 4.79; N, 16.66 Found: C, 49.87; H, 4.88; N, 16.53.

EXAMPLE IV

4-Amino-7,8,9,10-tetrahydro-6H-pyrido[1,2-a]azepin-2-one Monohydrate

To a solution of lithium diisopropylamide (LDA), prepared from n-BuLi (125 ml, 0.2M) and diisopropylamine (20.2 g, 28.1 ml, 0.2M) in dry THF (100 ml) was added under $N_2$ at $-30°$ to $-10°$ C., 5-methylisoxazole (8.3 g, 0.1M). The resultant yellow suspension was mechanically stirred at $-10°$ C. for 1 hr before 1-aza-2-methoxy-1-cycloheptene (12.7 g, 0.1M) was added dropwise. After the addition was complete, a yellow solid separated and the mixture was allowed to warm to ambient over a period of 19 hr. Then dry MeOH (50 ml) was slowly added and the resultant reddish solution was vigorously stirred at ambient for 2 hr and filtered through a silica gel pad. The filtrate was evaporated in vacuo, and the residual oil was flash column chromatographed on silica gel (EM-60) with 30% MeOH in $CH_2Cl_2$ as the eluent to give the desired amine, which was further recrystallized from MeOH/Et$_2$O to give the title compound (5.75 g, 30%), mp>230° C. TLC (30% MeOH in $CH_2Cl_2$): Rf=0.40. IR (KBr) cm$^{-1}$, 3400–3200 (broad), 1660, 1635.

Anal. Calcd for $C_{10}H_{14}N_2O \cdot H_2O$: C, 61.19; H, 8.22; N, 14.28. Found: C, 60.70; H, 8.28; N, 14.07.

EXAMPLE V

4-Amino-7,8,9,10-tetrahydro-6H-pyrido[1,2-a]azepin-2-one Monohydrochloride

A solution of the product of Example IV (3.3 g, 16.8 mM) in MeOH (20 ml) was acidified (pH 1) with conc HCl, evaporated in vacuo, and diluted with acetone to give the title compound (3.6 g, 100%), mp>230° C., TLC (30% MeOH in $CH_2Cl_2$): $R_f$=0.46. IR (KBr) cm$^{-1}$, 3300, 3140, 3000, 1660, 1640, 1590.

Anal. Calcd for $C_{10}H_{14}N_2O \cdot HCl$: C, 55.94; H, 7.04; N, 13.05. Found: C, 55.73; H, 7.14; N, 12.99.

EXAMPLE VI 6,7,8,9-Tetrahydro-4-(N,N-dimethylamino)quinolizin-2-one

To a mixture of NaH (2.2 g, 50% in oil, 45 mM) washed free of oil with pentane, and dry THF (30 ml) was added portionwise under $N_2$ at ambient the product of Example II (2.97 g, 15 mM). The resultant mixture was stirred for 30 min and methyl iodide (1.9 ml, 30 mM) was added dropwise while the reaction mixture was cooled in an ice-water bath. When the addition was completed, the ice-water bath was removed and the mixture was kept in a refrigerator for 24 hours. The brownish mixture was then poured onto ice and the aqueous mixture was saturated with NaCl and extracted with $CH_2Cl_2$ (5×50 ml). The combined extract was washed with water followed by brine, dried (MgSO$_4$), filtered, evaporated in vacuo, and flash column chromatographed silica gel (EM-60), Et$_2$O: MeOH:$CH_2Cl_2$/1:2:7) to give crude product (3.2 g, 100%). Recrystallization from $CH_2Cl_2$:ether gave the title compound (2.0 g), mp 72°–76° C. TLC (Et$_2$O:-MeOH:$CH_2Cl_2$/1:2:7); $R_f$=0.53. IR (KBr) cm$^{-1}$, 1630, 1530.

Anal. Calcd for $C_{11}H_{16}N_2O$: C, 68.71; H, 8.39; N, 14.57. Found: C, 67.83; H, 8.35; N, 14.57.

EXAMPLE VII 6,7,8,9-Tetrahydro-4-(N,N-dimethylamino)quinolizin-2-one Monohydrochloride To a solution of the product of Example VI (1.6 g, 8.3 mM) in MeOH (50 ml) was added dropwise with stirring concentrated HCl (pH was checked by pH paper). The resultant solution was filtered and evaported in vacuo to give the desired hydrochloride salt. Recrystallization from MeOH/acetone gave the title compound (1.5 g, 79%); mp 182°–184° C.; TLC (10% MeOH in $CH_2Cl_2$) $R_f$=0.66; IR (KBr) cm$^{-1}$: 3200, 2460, 1620.

Anal. Calcd for $C_{11}H_{16}N_2O \cdot HCL$: C, 57.76; H, 7.49; N, 12.25. Found: C, 57.19; H, 7.50, N, 12.27.

Example VIII 6,7,8,9-Tetrahydro-4-(N,N-dimethylaminomethylenamino)-quinolizin-2-one 1/3 Hydrate A mixture of 4-amino-6,7,8,9-tetrahydroquinolizin-2-one (1.56 g, 9.5 mM) and N,N-dimethylformamide dimethylacetal (3.4 g, 28.5 mM) in CH$_3$OH (20 ml) was stirred at reflux under $N_2$ for 2 hours, cooled to ambient, and evaporated in vacuo. The residual semi-solid was dissolved in $CH_2Cl_2$ (50 ml) and treated with charcoal (Nuchar S-N). Recrystallization from $CH_2Cl_2$/Hexane gave the title compound (1.4 g, 67%), mp 190°–193° C. TLC (30% MeOH in $CH_2Cl_2$) $R_f$=0.59 IR(KBr) 3300, 2930, 1630 cm$^{-1}$.

Anal. Calcd for $C_{12}N_{17}N_3O \cdot \frac{1}{3} H_2O$: C, 63.97; H, 7.91; N, 18.65. Found: C, 63.88; H, 7.51; N, 8.44.

Example IX

7,8,9,10-Tetrahydro-4-(N,N-dimethylaminomethylenamino)-6H-pyrido[1,2-a]azepin-2-one 1/10 Hydrate A mixture of 4-amino-7,8,9,10-tetrahydro-6H-pyrido[1,2-a]-azapin-2-one (1.85 g, 10.4 mM) and N,N-dimethylformamide dimethylacetal (3.7 g, 4.1 ml, 31.1 mM) in MeOH (25 ml) was stirred at reflux under $N_2$ for 1 hour, cooled to ambient, and evaporated in vacuo. The residual semi-solid was dissolved in $CH_2Cl_2$ (50 ml) and treated with charcoal (Nuchar S-N). Crystallization from $CH_2Cl_2$/Hexane give the title compound (1.93 g, 79.5%), mp 174°–176° C. TLC (30% MeOH in $CH_2Cl_2$): $R_f = 0.71$ IR(KBr) 1620 cm$^{-1}$.

Anal. Calcd for $C_{13}H_{19}N_3O \cdot 1/10 H_2O$: C, 66.41; H, 8.23; N, 17.87. Found: C, 66.05; H, 8.32; N, 17.75.

EXAMPLE X

7,8,9,10-Tetrahydro-4-(N,N-dimethylamino)-6H-pyrido[1,2-a]azepin-2-one Monohydrochloride 1/10 Hydrate To a predried three-neck bottom flask was added under $N_2$, NaH (1.5 g, 50% dispersion in oil., 31.3 mM). The NaH was washed free of oil with pentane (5×7 ml), dried with a stream of $N_2$ and covered with dry THF (40 ml). 4-Amino-7,8,9,10-tetrahydro-6H-pyrido[1,2-a]azapin-2-one (2.8 g, 15.6 mM) was added. The resultant mixture was stirred at ambient under $N_2$ for 2 hours, cooled in an ice-$H_2O$ bath, and $CH_3I$ (4.4 g, 1.9 ml, 31.25 mM) was added. The mixture was slowly warmed up to ambient, stirred at ambient for 2 hours, poured into ice $H_2O$ (250 ml) and extracted with $CH_2Cl_2$ (1×300 ml). The $H_2O$ layer was saturated with NaCl and extracted further with $CH_2Cl_2$ (1×300 ml). The combined $CH_2Cl_2$ extract was dried ($MgSO_4$), evaporated in vacuo to give the free base as a semisolid (3.1 g). The HCl salt was prepared by adding concentrated HCl to a solution of the free base in MeOH (60 ml). Recrystallization from $CH_2Cl_2$/$Et_2O$ gave the title compound (3.1 g, 81%), mp 208°–210° C. TLC (10% MeOH in $CH_2Cl_2$): $R_f = 0.46$; IR(KBr) 3270, 2440, 1630 cm$^{-1}$.

Anal. Calcd for $C_{12}H_{18}N_2O \cdot HCl$: C, 59.37; H, 7.89; N, 11.54. Found: C, 58.90; H, 7.80; N, 11.43.

EXAMPLE XI

2,3-Dihydro-5-(N,N-dimethylaminomethylenamino)-thiazolo-[3,2-a]pyridin-7-one ¼ Hydrate A mixture of 5-amino-2,3-dihydrothiazolo[3,2-a]pyridin-7-one (2.0 g, 12 mM) and N,N-dimethylformamide dimethylacetal (4.2 g, 4.7 ml, 35.7 mM) in MeOH (25 ml) was stirred at reflux under $N_2$ for ½ hour, cooled to ambient, and evaporated in vacuo. The residual semi-solid was flash column chromatographed (silica gel, EM-60, 30% MeOH in $CH_2Cl_2$). Crystallization from MeOH/$Et_2O$ gave the title compound (0.89 g, 33.2%), mp 178°–182° C. TLC (30% MeOH in $CH_2Cl_2$): $R_f = 0.74$; IR(KBr) 3345, 1630 cm$^{-1}$.

Anal. Calcd for $C_{10}H_{13}N_3OS \cdot \frac{1}{4} H_2O$: C, 52.72; H, 5.97; N, 18.44. Found: C, 52.23; H, 5.72; N, 18.16.

EXAMPLE XII

6-Amino-1,4-dihydro-1,2-dimethylpyridin-4-one Monohydrochloride

To a solution of lithium diisopropylamide (LDA), prepared from n-BuLi (77.5 ml, 120 mM) and diisopropylamine (12.2 g, 17 ml, 120 mM) in dry THF (100 ml) was added under $N_2$ at −30° to −10° C., 5-methylisoxazole (5g, 60 mM). The resultant yellow suspension was mechanically stirred at −10° C. for 1 hr. before ethyl N-methylacetimidate (6g, 60 mM) was added dropwise. The resultant orange suspension was stirred at ambient for 19 hr and then quenched with dry MeOH (50 ml) to give a homogeneous solution which was stirred at ambient for 5 hr. After evaporation in vacuo, the residual oil was flash column chromatographed on silica gel (EM-60), with 30% MeOH in $CH_2Cl_2$ as the eluent to give the crude product. Recrystallization from MeOH/acetone gave the free base of the title compound (1.5 g, 18%).

A solution of the free base (1.5 g, 10.9 mM) in MeOH (20 ml) was acidified with concentrated HCl (pH 1), evaporated in vacuo, solidified by adding acetone and recrystallized from MeOH/acetone to give the title compound (1.57 g, 82.5%), mp>250° C. TLC (30% MeOH in $CH_2Cl_2$): $R_f = 0.37$. IR(KBr), 3300, 3150, 1650, 1590 cm$^{-1}$.

Anal. Calc'd for $C_7H_{10}N_2O \cdot HCl$: C, 48.14; H, 6.35; N, 16.0. Found: C, 47.90; H, 6.23; N, 16.0.

EXAMPLE XIII

2,3-Dihydro-5-(N,N-dimethylacetamidino)-1(H)-indolizin-7-one ¼ Hydrate

To a solution of 5-amino-2,3-dihydro-1H-indolizin-7-one (1.6 g, 10.6 mM) in $CH_3OH$ (40 ml) was added N,N-dimethylacetamide dimethylacetal (4.3 g, 4.8 ml, 31.9 mM) under $N_2$. The resultant solution was stirred at reflux under $N_2$ for ½ hours, cooled to ambient, evaporated in vacuo and flash column chromatographed (silica Gel,EM-60; 30% MeOH in $CH_2Cl_2$) to give impure title compound. Recrystallization from $CH_2Cl_2$/$Et_2O$ gave the title compound as an off-white crystalline solid, mp 134°–136° C. TLC (30% $CH_3OH$ in $CH_2Cl_2$): $R_f = 0.72$. IR(KBr), 3340, 1620 cm$^{-1}$.

Anal. Calc'd for $C_{12}H_{17}N_3O \cdot \frac{1}{4} H_2O$: C, 64.60; H, 7.88; N, 18.78. Found: C, 64.31; H, 7.77; N, 18.62.

EXAMPLE XIV

1,4-Dihydro-6-(N,N-dimethylformamidino)-1,2-dimethyl pyridin-4-one

A mixture of 6-amino-1,4-dihydro-1,2-dimethylpyridin-4-one (2 g, 14 mM) and N,N-dimethylformamide dimethylacetal (5.2 g, 6 ml, 43 mM) in $CH_3OH$ (50 ml) was stirred at reflux under $N_2$ for 45 min., cooled to ambient and evaporated in vacuo to give the title compound as a semisolid. Recrystallization from $CH_2Cl_2$/$Et_2O$ gave the title compound as an off-white crystalline solid (2.5 g, 92%). mp 176°–180° C. TLC ($CH_2Cl_2$MeOH:$Et_2O$; 7:2:1) $R_f = 0.61$. IR(KBr) 3440, 1650 cm$^{-1}$.

Anal. Calc'd for $C_{10}H_{15}N_3O$: C, 62.15; H, 7.82; N, 21.74. Found: C, 61.81; H, 7.84; N, 21.68.

EXAMPLE XV

3-Benzyl-4-(N,N-dibenzylamino)-7,8,9,10-tetrahydro-6H-pyrido[1,2-a]azepin-2-one Monohydrochloride To a suspension of NaH (1.6 g, 50% dispersion in oil, 33.7 mM) washed free of oil with pentane (5×10 ml) then dried with a stream of $N_2$, in dry THF (60 ml) was added 4-amino-7,8,9,10-tetrahydro-6H-pyrido[1,2-a]azepin-2-one (3 g, 16.8 mM). The resultant mixture was stirred at ambient under $N_2$ for 2 hours, cooled in an ice-$H_2O$ bath, and benzyl bromide (5.8 g, 4 ml, 33.7 mM) was added. The mixture was slowly warmed up to ambient, stirred at ambient for 1½ hours, filtered through Celite eluting further with $CH_2Cl_2$, evaporated in vacuo and flash column chromatographed (silica gel 25-40 mm; 2% MeOH in $CH_2Cl_2$) to give a solid, free base (1.2 g, 18%). The HCl salt was prepared by adding conc. HCl to the free base in MeOH. Recrystallization from MeOH/acetone gave the title compound (0.9 g, 61%), mp 245°-249° C. TLC (2% MeOH in $CH_2Cl_2$) $R_f=0.18$; IR(KBr) 3420, 2440, 1620 $cm^{-1}$.

Anal. Calc'd for $C_{31}H_{32}N_2O \cdot HCl$: C, 76.76; H, 6.86; N, 5.78. Found: C, 76.46; H, 7.10; N, 5.65.

EXAMPLE XVI

2,3-Dihydro-5-(N,N-dimethylacetamidino)thiazolo[3,2-a]pyridin-7-one

A mixture of 5-amino-2,3-dihydrothiazolo[3,2-a]pyridin-7-one (3 g, 17.8 mM) and N,N-dimethylacetamide diethylacetal (7.1 g, 7.8 ml, 54 mM) in $CH_3OH$ (60 ml) was stirred at reflux under $N_2$ for ½ hours, cooled to ambient, evaporated in vacuo, and flash column chromatographed (Silica Gel 25-40 mm; $CH_2Cl_2$:$CH_3OH$:$Et_2O$; 70:20:10) to give a semi-solid. Recrystallization of the semi-solid from $CH_2Cl_2/Et_2O$ gave the title compound as a white crystalline solid (1.9 g, 45%), mp 148°-151° C. TLC ($CH_2Cl_2$:$CH_3OH$:$Et_2O$; 7:2:1) $R_f=0.55$. IR(KBr) 3420, 2920, 1600 $cm^{-1}$.

Anal. Calc'd for $C_{11}H_{15}N_3OS$: C, 55.67; H, 6.37; 17.71. Found: C, 55.12; H, 6.33; 17.65.

EXAMPLE XVII

2,3-Dihydro-5-(N,N-dimethylamino)thiazolo[3,2-a]pyridin7-one Monohydrochloride ¼ Hydrate To a suspension of NaH (1.2 g, 50% dispersion in oil, 24 mM) washed free of oil with pentane (5×10 ml) then dried with a stream of $N_2$, in dry THF (60 ml) was added 5-amino-2,3-dihydrothiazolo[3,2-a]pyridin-7-one (2 g, 12 mM) under $N_2$. The resultant mixture was stirred at ambient for 2 hours, cooled in an ice-$H_2O$ bath and MeI (3.4 g, 1.5 ml, 24 mM) was added. The mixture was slowly warmed up to ambient, stirred at ambient for 16 hours, filtered through Celite, diluted with $CH_2Cl_2$ (200 ml) and washed with saturated $NaCl \cdot H_2O$ (150 ml). The $CH_2Cl_2$ extract was then dried ($MgSO_4$), filtered, evaporated in vacuo and flash column chromatographed (silica gel 25-40 mm, $CH_2Cl_2$:$CH_3OH$:$Et_2O$; 7:2:1) to give the free base. The HCl salt of the free base was prepared by adding concentrated HCl to the solution of the free base in MeOH. Recrystallization from MeOH/$Et_2O$ gave the title compound (1.37 g, 48%), mp 132°-135° C. TLC ($CH_2Cl_2$:MeOH:$Et_2O$; 7:2:1) $R_f=0.64$: IR(KBr) 2510, 1640 $cm^{-1}$.

Anal. Calc'd for $C_9H_{12}N_2OS \cdot HCl \cdot \frac{1}{4}H_2O$: C, 45.56; H, 5.73; N, 11.81. Found: C, 45.22; H, 5.52; N, 11.66.

EXAMPLE XVIII

7,8,9,10-Tetrahydro-4-(N,N-dipropylamino)-6H-pyrido[1,2-a]azepin-2-one Monohydrobromide To a suspension of NaH (1.0 g, 22 mM) washed free of oil with pentane (5×10 ml) then dried with a stream of $N_2$ in dry THF (60 ml) was added 4-amino-7,8,9,10-tetrahydro-6H-pyrido[1,2-a]azepin-2-one (2 g, 11 mM). The resultant mixture was stirred at ambient under $N_2$ for 2½ hours, and 1-iodopropane (3.8 g, 2 ml, 22 mM) was added. The mixture was stirred at ambient for 2 hours, filtered through Celite eluting further with 100 ml of $CH_2Cl_2$, and washed with $H_2O$ (1×200 ml). The aqueous layer was saturated with NaCl and extracted with $CH_2Cl_2$ (150 ml). The combined $CH_2Cl_2$ extract was dried ($MgSO_4$), filtered, evaporated in vacuo and flash column chromatographed (silica gel 25-40 mm; $CH_2Cl_2$:MeOH:$Et_2O$, 7:2:1) to give the free base, (1.5 g, 52%). The HBr salt of the free base was prepared by bubbling HBr gas into a solution of the free base in acetone. Recrystallization from EtOAc/$Et_2O$ at 5° C. gave the title compound as a white solid (0.52 g, 26%), mp 105°-109° C. TLC (10% $CH_3OH$ in $CH_2Cl_2$) $R_f=0.81$. IR(KBr) 2600, 1630 $cm^{-1}$:

Anal. Calcd for $C_{16}H_{26}N_2O \cdot HBr$: C, 55.97; H, 7.93; N, 8.16. Found: C, 55.92; H, 8.17; N, 8.06.

EXAMPLE XIX

4-Amino-7,8,9,10-tetrahydro-3-methyl-6H-pyrido[1,2-a]azepin-2-one Monohydrochloride To a solution of LDA (lithium diisopropylamide) prepared from diisopropylamine (40.5 g, 0.4M) and n-BuLi (hexane solution, 250 ml, 0.4M) in THF (300 ml) at −10° C., was added 4,5-dimethylisoxazole (19.4 g, 0.2M). The resultant solution was mechanically stirred at −10° C. for 1 hour, followed by the addition of 1-aza-2-methoxy-1-cycloheptene (25.4 g, 0.2 M). Then the mixture was stirred at −10° C. to ambient over a period of 20 hours, diluted with $CH_3OH$ (150 ml) at 10° C., stirred at ambient for 5 hours, and evaporated in vacuo. The brownish residue was flash column chromatographed on silica gel (40 mm, J. T. Baker) using 20% $CH_3OH$ in $CH_2Cl_2$ as the eluent to give a crude oil, which solidified upon stirring in acetone at ambient for 24 hours to give the free base (11.85 g, 30.8%). The free base (4.8 g, 25 mM) was treated with conc. HCl in MeOH to give the HCl salt which was recrystallized from MeOH/acetone to afford the title compound (4.63 g, 81%), mp>260° C. TLC (20% MeOH in $CH_2Cl_2$): $R_f=0.29$. IR(KBr) 3320, 3180, 2900, 2600, 1640, 1595 $cm^{-1}$.

Anal. Calc'd for $C_{11}H_{16}N_2O \cdot HCl$: C, 57.76; H, 7.50; N, 12.25. Found: C, 57.74; H, 7.56; N, 12.09.

EXAMPLE XX

7,8,9,10-Tetrahydro-3-methyl-4-(N,N-dimethylamino)-6H-pyrido[1,2-a]azepin-2-one Monohydrochloride To a suspension of NaH (2.88 g, 50% in oil, 60 mM) washed free of oil with pentane, in THF (100 ml) was added 4-amino-3-methyl-7,8,9,10-tetrahydro-6H-pyrido[1,2-a]azapin2-one (5.7 g, 30 mM) at ambient under $N_2$. The mixture was then stirred at ambient for 1.5 hours before $CH_3I$ (3.7 ml, 60 mM) was added portionwise. After stirring at ambient overnight, the mixture was evaporated in vacuo and flash column chromatographed on silica gel EM-60 using 10% $CH_3OH$ in CH$_2$Cl$_2$ as the eluent to give the free base (3 g, 45.4%). The free base (2 g, 9 mM) was dissolved in CH$_3$OH and treated with conc. HCl (aq) to afford the HCl salt which was further recrystallized from CH$_3$OH/acetone to give the title compound (1 g, 43.3%), mp 256°–257° C. (decomp). TLC (20% CH$_3$OH in CH$_2$Cl$_2$); R$_f$=0.68. IR(KBr), 2400, 1715, 1615 cm$^{-1}$.

Anal. Calc'd for C$_{13}$H$_{20}$N$_2$O.HCl: C, 60.80; H, 8.24; N, 10.91. Found: C, 60.45; H, 8.35; N, 10.75.

EXAMPLE XXI 4-(N,N-Diethylamino)-6,7,8,9,-tetrahydroquinolizin-2-one Monohydrobromide To a suspension of NaH (1 g, 50% dispersion in oil, 24 mM) washed free of oil with pentane (5×10 ml) then dried with a stream of N$_2$ in dry THF (50 ml) was added 4-amino-6,7,8,9-tetrahydroquinolizin-2-one (2 g, 12 mM). The resultant mixture was stirred at ambient for 2 hours and ethyl iodide (1.9 ml, 24 mM) was added. The mixture was stirred at ambient overnight, filtered through Celite (eluting further with MeOH), evaporated in vacuo, and flash column chromatographed (silica gel, EM-60; 10% MeOH in CH$_2$Cl$_2$) to give N-ethylamino (0.76 g, 33%) and N,N-diethylamino (1.5 g, 65%) products. The HBr salt of the latter product was prepared by bubbling HBr gas into a solution of the latter in acetone. Recrystallization from cold (5° C.) acetone gave the title compound as a white crystalline solid (0.55 g, 27%), m.p. 138°–141° C. TLC (10% CH$_3$OH in CH$_2$Cl$_2$), R$_f$=0.55. IR(KBr) 2760, 1630 cm$^{-1}$.

Anal. Calc'd for C$_{13}$H$_{20}$N$_2$O.HBr: C, 51.83; H, 7.03; N, 9.30. Found: C, 51.35; H, 7.07; N, 9.17.

EXAMPLE XXII

3-Bromo-7,8,9,10-tetrahydro-4-(N,N-dimethyl)-6H-pyrido [1,2-a]azepin-2-one Monohydrochloride A mixture of 4-(N,N-dimethylamino)-7,8,9,10-tetrahydro-6H-pyrido[1,2-a]azepin-2-one (1 g, 4.8 mM), N-bromosuccinimide (0.86 g, 4.8 mM) and benzoylperoxide (0.03 g) in CCl$_4$ (40 ml) was stirred at reflux under N$_2$ for 1 hour, cooled to ambient, evaporated in vacuo and flash column chromatographed (silica gel, EM-60, 10% MeOH in CH$_2$Cl$_2$) to give the free base (1.11 g, 80%). The HCl salt of the free base was prepared by addition of concentrated HCl to a solution of the free base in CH$_3$OH. Recrystallization from acetone gave the title compound as a white crystalline solid (1.2 g, 97%). mp. 209°–210° C. (decomposed). TLC (10% MeOH in CH$_2$Cl$_2$):R$_f$=0.62; IR(KBr) 3400, 2300, 1720 cm$^{-1}$.

Anal. Calc'd for C$_{12}$H$_{17}$BrN$_2$O.HCl: C, 44.80; H, 5.64; N, 8.71. Found: C, 44.54; H, 5.79; N, 8.48.

EXAMPLE XXIII 4-(N,N-Diallyl-1-oxoamino)-7,8,9,10-tetrahydro-6H-pyrido [1,2-a]azepin-2-one To a suspension of NaH (1 g, 22 mM) washed free of oil with pentane (5×10 ml) then dried with a stream of N2, in dry THF (50 ml) was added 4-amino-7,8,9,10-tetrahydro-6H-pyrido[1,2-a]azepin-2-one (2 g, 11 mM) under N$_2$. The resultant mixture was stirred at ambient under N$_2$ for 1.5 hr. and allylbromide (2.7 g, 1.9 ml, 22 mM) was added. The mixture was stirred at ambient for 2 hr., poured into ice-H$_2$O (200 ml) and extracted with CH$_2$Cl$_2$ (1×250 ml). The aqueous layer was saturated with NaCl and extracted further with CH$_2$Cl$_2$ (250 ml). The combined CH$_2$Cl$_2$ extract was dried (MgSO$_4$), evaported in vacuo, and flash column chromatographed (silica gel, EM-60; CH$_2$Cl$_2$:MeOH:Et$_2$O, 6:1:3) to give 4-(N,N-diallylamino)-7,8,9,10-tetrahydro-6H-pyrido[1,2-a]azepin-2-one (2.1 g, 37%).

To a solution of 4-(N,N-diallylamino)-7,8,9,10-tetrahydro-6H-pyrido[1,2-a]azepin-2-one (1.9 g, 7.4 mM) in CH$_2$Cl$_2$ (100 ml) was added m-CPBA (7.6 g, 44 mM). The resultant mixture was stirred at ambient for 48 hours, cooled in an ice-H$_2$O bath and 5% Na$_2$SO$_3$/H$_2$O solution was slowly added over a period of 15 min. The mixture was then filtered through Celite eluting further with CH$_2$Cl$_2$, washed with saturated NaHCO$_3$-H$_2$O (1×150 ml), then with saturated NaCl.H$_2$O (1×150 ml), dried (MgSO$_4$), filtered and evaporated in vacuo. The residual oil was flash column chromatographed (silica gel, EM-60, CH$_2$Cl$_2$:Et$_2$O:CH$_3$OH, 7:2:1) to give a semi-solid (640 mg, 35%). Recrystallization of the semi-solid from acetone gave the title compound as an off-white crystalline solid. mp. 172°–175° C. TLC (10% CH$_3$OH in CH$_2$Cl$_2$) R$_f$=0.60; IR(KBr) 2850, 1610 cm$^{-1}$.

Anal. Calc'd for C$_{16}$H$_{22}$N$_2$O$_2$: C, 70.04; H, 8.08; N, 10.21. Found: C, 69.57; H. 8.02; N, 10.01.

EXAMPLE XXIV 6,7,8,9-Tetrahydro-4-(N,N-dimethylacetamidino)-quinolizin-2-one Hemihydrate A mixture of 4-amino-6,7,8,9-tetrahydroquinolizin-2-one (2.0g, 12 mM) and N,N-dimethylacetamide diethylacetal (4.8 g, 5.3 ml, 36 mM) in CH$_3$OH (50 ml) was stirred at reflux under N$_2$ for 3 hr, evaporated in vacuo, trituated with Et$_2$O, filtered, and washed with Et$_2$O to give a crude solid product. Recrystallization from CH$_2$Cl$_2$/Et$_2$O gave the title compound (1.73 g, 61.87%), mp 127°–130° C. TLC (10% MeOH in CH$_2$Cl$_2$). R$_f$=0.32; IR (KBr) 3400–3100, 1610, 1520, cm$^{-1}$.

Anal. Calcd for C$_{13}$H$_{19}$N$_3$O ½ H$_2$O: C, 64.43; H, 8.32; N, 17.34. Found: C, 64.81; H, 8.13; N, 17.36.

EXAMPLE XXV

4-Amino-6,7,8,9-tetrahydro-3-methylquinolizin-2-one Monohydrochloride

To a solution of lithium diisopropylamide (LDA), prepared from n-BuLi (1.6M in hexane, 387 ml, 0.62M) and diisopropylamine (86 ml, 0.62M) in dry THF (350 ml) was added under N$_2$ at −10° C. 4,5-dimethylisoxazole (30 g, 0.31M). The resultant yellow suspension was stirred at −10° C. for 1.5 hr and 1-aza-2-methoxy-1-cyclohexene (35 g, 0.31M) was added dropwise. The mixture was slowly warmed up to ambient, stirred at ambient for 12 hours, cooled in an ice-H$_2$O bath and was treated with MeOH (350 ml). The resulting reddish solution was stirred at ambient for 2 hr., evaporated in vacuo and flash column chromatographed (silica gel, EM-60, 30% CH$_2$OH in CH$_2$Cl$_2$) to give the desired free base (15.7 g, 28%).

The HCl salt was prepared by the addition of concentrated HCl to a solution of the free base (1.23 g, 6.9 mM) in methanol. Recrystallization from MeOH/acetone gave the title compound (1.3 g, 88%), m.p. >240° C. TLC (30% MeOH in CH$_2$Cl$_2$) R$_f$=0.48; IR (kBr) 3320, 3160, 1650 cm$^{-1}$.

Anal. Calc'd for C$_{10}$H$_{14}$N$_2$O HCl: C, 55.94; H, 7.04, N, 13.05. Found: C, 55.89.. H, 6.91; N, 12.97.

2,3-Dihydro-6-methyl-5-(N,N-dimethylamino)-
thiazolo[3,2-a]pyridin-2-one Monohydrochloride To a suspension of NaH (1.3 g, 60 dispersion in oil, 33 mM) washed free of oil with pentane (5×5 ml) then dried with a stream of N₂, in dry THF (60 ml) was added 5-amino-2,3-dihydro-6-methylthiazolo[3,2-a]pyridin-2-one (3 g, 16.5 mM). The resultant mixture was stirred at ambient under N₂ for 2.5 hr, and MeI (4.7 g, 2.0 ml, 33M) was added. The mixture was stirred at ambient for 72 hrs., filtered through Celite eluting further with CH₂Cl₂, evaporated in vacuo, and flash column chromatographed (silica gel, EM-60, 10% CH₃OH in CH₂Cl₂) to give the desired free base (1.4 g, 40%). The HCl salt was prepared by dropwise addition of conc. HCl to a solution of the free base in MeOH (pH checked by PH paper). Recrystallization from MeOH-/acetone gave the title compound (0.9 g, 55%), mp >240° C. TLC (10% MeOH in CH₂Cl₂) R$_f$=0.54. IR (KBr) 2800, 2500, 1600 cm$^{-1}$.

Anal. Calc'd for C$_{10}$H$_{14}$N$_2$OS.HCl: C, 48.67, H, 6.13; N, 11.35. Found: C, 48.16; H, 5.77; N, 11.10.

EXAMPLE XXVII 5-(N,N-Diacetylamino)-2,3-dihydrothiazolo[3,2-a]pyridin-2-one

A mixture of 5-amino-2,3-dihydrothiazolo[3,2-a]pyridin-2-one (6 g, 36 mM) and acetic anhydride (60 ml, 640 mM) was stirred at reflux under N₂ for 1 hr., cooled to ambient, and poured into Et₂O (500 ml) with stirring. The solid material was filtered and flash column chromatographed (silica gel, EM-60, 10% EtOH in CH₂Cl₂) to give N-acetylamino and N,N-diacetylamino products. Recrystallization of these products from CH₃OH/acetone gave off-whie crystalline solids of the former product (3.2 g, 42%) and the title product (2.78 g, 31%), M.P. 202–203° C. (decomposed). TLC (10% CH₃OH in CH₂Cl₂): R$_f$=0.32. IR (KBr) 1760, 1715, 1620, cm$^{-1}$.

Anal. Calc'd for C$_{11}$H$_{12}$N$_2$O$_3$S: C, 52.36; H, 4.80; N, 11.11. Found: C, 52.22; H, 4.70; N, 10.82.

EXAMPLE XXVIII

4-Acetamido-7,8,9,10-tetrahydro-6H-pyrido[1,2-a]azepin-2-one

A mixture of 4-amino-7,8,9,10-tetrahydro-6H-pyrido[1,2-a]azepin-2-one (2.77 g, 15.6 mM) and acetic anhydride (10 ml) was stirred at reflux under N₂ for 1.5 hr., poured into Et₂O (300 ml), stirred at ambient for 1 hr., and filtered to give a crude solid. Flash column chromatography (silica gel, EM-60, 8% CH₃OH in CH₂Cl₂) gave first the N,N-diacetylamino- and then the acetamido products. Recrystallization of the latter product furnished the title compound (1–5 g, 43.7%), m.p.>230° C. TLC (10% CH₃OH in CH₂C₂): R$_f$=0.24. IR (KBr) 3150, 1700, 1630 cm$^{-1}$.

Anal. Calc'd for C$_{12}$H$_{16}$N$_2$O$_2$: C, 65.45; H, 7.32; N, 12.72. Found : C, 65.11; H, 7.81; N, 12.48.

EXAMPLE XXIX 6,7,8,9-Tetrahydro-3-methyl-4-(N,N-dimethylamino)-quinolizin-2-one To a suspension of NaH (1.3 g, 34 mM, 60% dispersion in oil) washed free of oil with pentane (5×5 ml) then dried with a stream of N₂, in dry THF (80 ml), was added 4-amino-6,7,8,9-tetrahydro-3-methylquinolizin-2-one (3 g, 16.8 mM). The resultant mixture was stirred at ambient under N₂ for 2 hrs and CH₃I (2 ml, 34 mM) was added. The mixture was stirred at ambient for 1.5 hrs, filtered through a celite pad eluting further with CH₂Cl₂, evaporated in vacuo and flash column chromatographed (silica gel, EM-60, 10% CH₃OH in CH₂Cl₂) to give the dimethylamino (0.9 g, 22%) and the monomethylamino(2.6 g, 80%) products. The former product was converted into HCl salt by concentrated HCl in CH₃OH. Recrystallization from MeOH/acetone gave the title compound (360 g, 58%), m.p. >240° C. TLC (10% CH₃OH in CH₂Cl₂): R$_f$=0.52 IR(KBr) 2800, 2620, 1625 cm$^{-1}$.

Anal. Calc'd for C$_{12}$H$_{18}$N$_2$O HCl: C, 59.37; H, 7.89; N, 11.54. C, 58.85; H, 7.63; N, 11.20.

EXAMPLE XXX 7,8,9,10-Tetrahydro-4-(N,N-dimethylacetamidino)-6H-pyrido[1,2-a]azepin-2-one A mixture of 4-amino-7,8,9,10-tetrahydro-6H-pyrido[1,2-a]azepin-2-one (5.3 g, 30 mM) and N,N-dimethylacetamide dimethylacetal (12 g, 13.2 ml, 90 mM) in absolute CH₃OH (50 ml) was stirred under N₂ at reflux for 2 hrs, cooled to ambient, concentrated in vacuo, trituated with Et₂O, filtered, rinsed with Et₂O, and crystallized from CH₂Cl₂/Et₂O to give the crude product (4.6 g, 62%). Recrystallization of the crude product three times from CH₂Cl₂/Et₂O provided the pure title compound, m.p. 116°–119° C. TLC (30% CH₃OH in CH₂Cl₂): R$_f$=0.38. IR (KBr) 3400, 3150, 2940, 1610, 1530, cm$^{-1}$.

The preceding Examples have been provided only for illustration of the subject invention and not to limit its scope, which is described only in the appended claims.

What is claimed is:

1. A compound having the formula

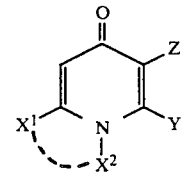

and the pharmaceutically acceptable acid addition salts and stereochemically isomeric forms thereof, wherein:

X$^1$ and X$^2$ are individually each loweralkyl or together as —X$^1$—X$^2$— are —(CH$_2$)$_n$— or —S(CH$_2$)$_m$—;

n is 3, 4, or 5;

m is 2 or 3;

Y is amino, loweralkylamino, diloweralkylamino, amido, loweralkyloxy amido, ureido, di(phenyl-loweralkyl) amino, (diloweralkylamino)methylenamino, or (diloweralkylamino)loweralkyl-methylenamino; and Z is hydrogen, loweralkyl, halo, or phenylloweralkyl.

2. The compound of claim 1 wherein Y is amino and Z is hydrogen.

3. The compound of claim 1 wherein X$^1$ and X$^2$ are each loweralkyl.

4. The compound of claim 3 wherein Y is NH$_2$.

5. The compound of claim 1 wherein —X$^1$—X$^2$— is —S(CH$_2$)$_m$—.

6. The compound of claim 5 wherein m is 2.

7. The compound of claim 6 wherein Y is (diloweralkylamino)methylenamino or (diloweralkylamino)-loweralkylmethylenamino.

8. The compound of claim 5 wherein Y is amino.

9. The compound of claim 1 wherein $-X^1-X^2-$ is $-(CH_2)_n-$.

10. The compound of claim 9 wherein n is 4 or 5 and Y is amino or diloweralkylamino.

11. The compound of claim 10 wherein Y is amino.

12. The compound of claim 10 wherein Z is loweralkyl.

13. The compound of claim 1, wherein $-X^1-X^2-$ is $-S(CH_2)_m-$ or $-(CH_2)_n-$.

14. The compound 4-amino-7,8,9,10-tetrahydro-6H-pyrido[1,2-a]azepin-2-one and its pharmaceutically acceptable acid addition salts and stereochemically isomeric forms.

15. The compound 4-amino-7,8,9,10-tetrahydro-3-methyl-6H-pyrido[1,2-a]azepin-2-one and its pharmaceutically acceptable acid addition salts and stereochemically isomeric forms.

16. A method of treating hypertension in a warm-blooded animal suffering from hypertension which comprises administering to said animal an effective antihypertensive amount of a compound of claim 1.

17. A method of treating bronchial asthma in a warm-blooded animal suffering from bronchial asthma which comprises administering to said animal an effective anti-asthma amount of a compound of claim 1.

18. An anti-hypertensive or anti-asthma composition comprising an effective amount of a compound of claim 1 in admixture with a pharmaceutically-acceptable carrier.

* * * * *